United States Patent [19]
Igushi

[11] Patent Number: 5,936,729
[45] Date of Patent: Aug. 10, 1999

[54] PHOTO DETECTOR ASSEMBLY FOR MEASURING PARTICLE SIZES

[75] Inventor: Tatsuo Igushi, Miyanohigashi-machi, Japan

[73] Assignee: Horiba, Ltd., Kyoto, Japan

[21] Appl. No.: 08/823,605

[22] Filed: Mar. 25, 1997

[30] Foreign Application Priority Data

Mar. 26, 1996 [JP] Japan .................................. 8-096064

[51] Int. Cl.$^6$ .................................................. G01N 15/02
[52] U.S. Cl. ........................... 356/336; 356/343; 250/574
[58] Field of Search .................................. 356/335–343, 356/39, 73; 250/574

[56] References Cited

U.S. PATENT DOCUMENTS

| | | | |
|---|---|---|---|
| 3,310,680 | 3/1967 | Hasegawa | 356/343 |
| 3,830,569 | 8/1974 | Meric | 356/336 |
| 3,873,206 | 3/1975 | Wilcock | 356/336 |
| 4,037,964 | 7/1977 | Wertheimer et al. | 356/336 |
| 4,167,335 | 9/1979 | Williams | 356/336 |
| 4,188,121 | 2/1980 | Hirleman, Jr. et al. | 356/336 |
| 4,274,741 | 6/1981 | Cornillault | 356/343 |
| 4,953,978 | 9/1990 | Bott et al. | 356/336 |

*Primary Examiner*—Hoa Q. Pham
*Attorney, Agent, or Firm*—Price Gess & Ubell

[57] ABSTRACT

An improved photo detector assembly for a particle size distribution measuring equipment provides a unitary opaque coating deposited above a photo detector layer with a plurality of concentric apertures that can be defined with high precision about a concentric center. The masking can be applied in a production environment to ensure high accuracy and a compact size.

10 Claims, 4 Drawing Sheets

PHOTO DETECTOR ASSEMBLY FOR MEASURING PARTICLE SIZES

BACKGROUND OF THE INVENTION

1. Field of the Invention

The present invention relates to a photo detector for irradiating a sample with a light source light and detecting the scattered light with a row of space light receiving elements, and belongs to the technical field of equipment for measuring a particle size distribution in a sample.

2. Description of Related Art

A diffracted light (scattered light) detector in which a plurality of light receiving elements such as photo diodes formed as circular arcs are arranged in a fan shape about a concentric circle is disclosed, for example, in Japanese Patent Publication No. Hei 2-145940.

The cross section of the light receiving element is shown, for example, in FIG. 4, where numeral 1 denotes a P layer in which the positive charge collects, numeral 2 the N layer in which the negative charge collects, numeral 3 the N+ layer, numeral 4 a depletion layer, numeral 5 a positive electrode, numeral 6 a transmittable insulation layer, and numeral 7 a negative electrode. The intensity of light received in the above-mentioned P layer 1 is taken out as a meassurement in the form of photoelectric current from the positive electrode 5.

The above-mentioned P layer 1 constitutes each light receiving element b, c, d, ... which is, in general, formed in oblong circular arcs in which each light receiving element is arranged on a concentric circle to form a fan shape (see FIG. 5), and photoelectric current corresponding to the light intensity in accord with each scattering angle is detected. The light receiving element a at the center portion detects the transmitted light.

On the circumferential portion of the P layer 1, a depletion layer 4 is formed but the shape of depletion layer 4 is extremely difficult to establish from the viewpoint of manufacturing, and the interface 1a between the P layer 1 and depletion layer 4 is usually formed inclined so as to spread in front. In the interface 1a, it is difficult to establish a precise shape, and about several μm manufacturing errors tend to occur during production.

When the shape accuracy of the interface 1a of P layer 1 is low, the accuracy of the arrangement condition between light receiving elements, for example, the accuracy of the isolation gap and alignment or the accuracy of effective light receiving area of each light receiving element degrades, causing a problem in that a high measurement accuracy cannot obtained.

Because it becomes difficult to arrange high shape accuracy light receiving elements at the position near the center portion, the measurement range of an area with small scattering angles is restricted, causing a problem in that the measurement range of a large-particle size area is limited, and it has been extremely difficult to expand the measuring area while achieving downsizing or higher accuracy.

OBJECTS AND SUMMARY OF THE INVENTION

In view of the foregoing, it is the main object of this invention to provide a photo detector which can expand the measuring area while achieving downsizing and higher accuracy.

This invention constructs a means for solving the above-mentioned problems as follows. That is, in a photo detector in which the sample is irradiated with the light source light and the scattered light is detected by a row of light receiving elements comprising a plurality of circular-arc-form light receiving elements arranged on a concentric circle, masking provided with an aperture for setting a specified light receiving area corresponding to each of the light receiving elements is applied to the light receiving surface of the light receiving element.

By applying a high processing accuracy masking to the light receiving surface, it becomes possible to set with a high accuracy the effective light receiving area of each light receiving element or isolation gap, alignment, etc. between the light receiving elements.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
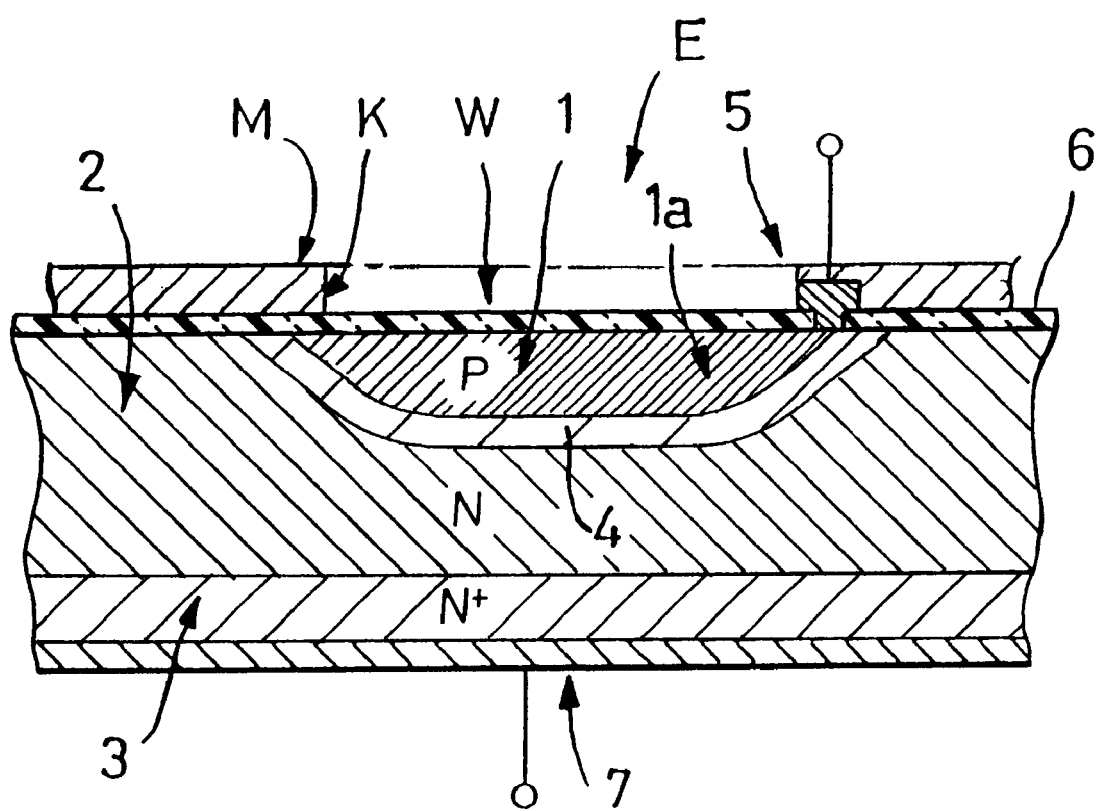
FIG. 1 is a cross-sectional view of a light receiving element showing one embodiment of a photo detector according to this invention.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an improved photo detector assembly for measuring particle sizes.

Referring now to the drawings, the embodiment of the present invention is described in detail as follows.

Figure 2:
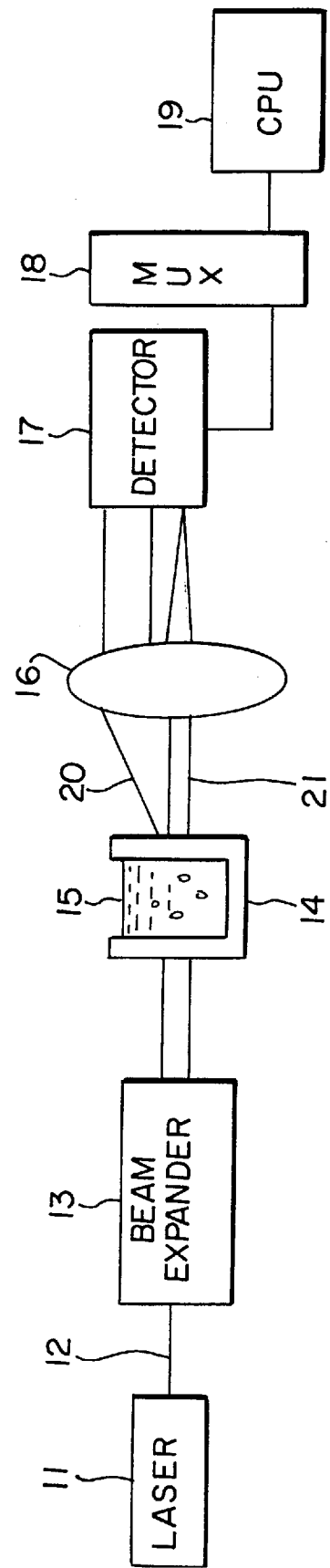
FIG. 2 is a block diagram of the particle size distribution measuring equipment of the above.

FIG. 2 shows the construction of principal portions of the particle size distribution measuring equipment, wherein numeral 11 is a laser tube as a light source for emitting a laser beam (light source light) 12, numeral 13 a beam expander for expanding laser beam 12 as required, numeral 14 a cell for storing sample 15, numeral 16 a condenser lens mounted behind the cell 14, numeral 17 a photo detector comprising photo diodes for detecting scattered light from the condenser lens 16, numeral 18 a multiplexer for taking in detection signals from the photo detector 17, numeral 19 a CPU to which signals from the multiplexer (MUX) 18 are inputted and which carries out a calculation of particle size distribution based on the scattered light intensity pattern.

In such particle size distribution measuring equipment, storing sample 15 in the cell 14 and irradiating the sample cell 14 with laser beam 12 irradiates particles in the sample 15 in the cell 14 with part of the laser beam 12 resulting scattered light 20, while the remainder of the light passes between the particles to make transmitted light 21. Scattered light 20 and transmitted light 21 reach the photo detector 17 via condenser lens 16.

Figure 3:
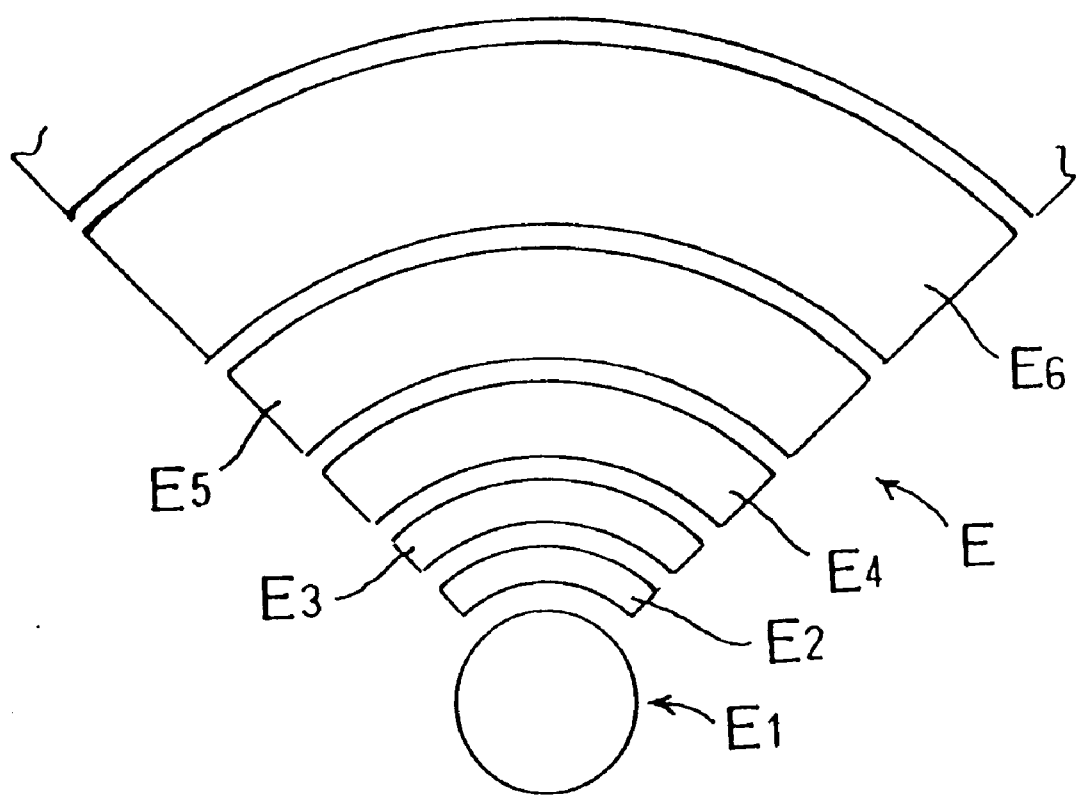
FIG. 3 is a plan view showing the arrangement of light receiving elements of FIG. 2.
Figure 4:
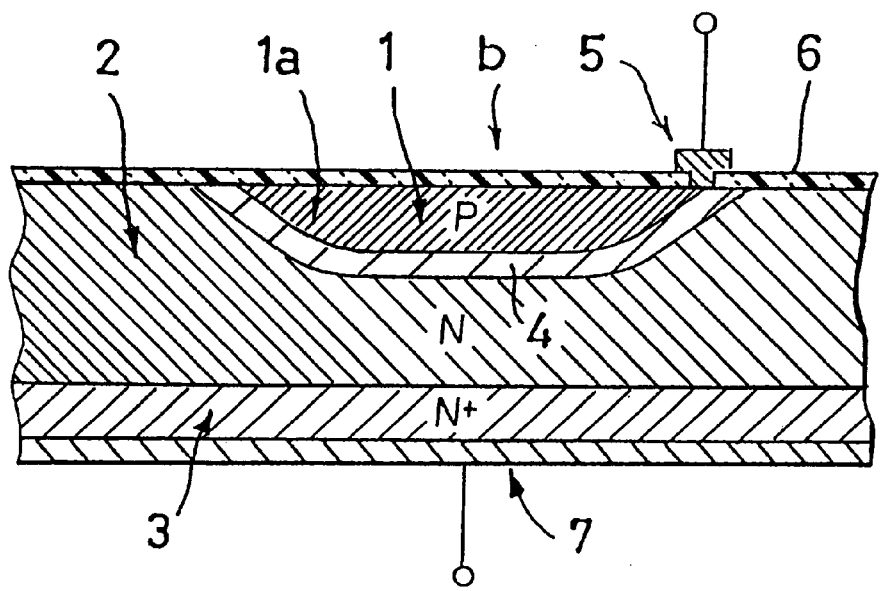
FIG. 4 is one example of a cross-sectional view showing a light receiving element in a conventional photo detector.
Figure 5:
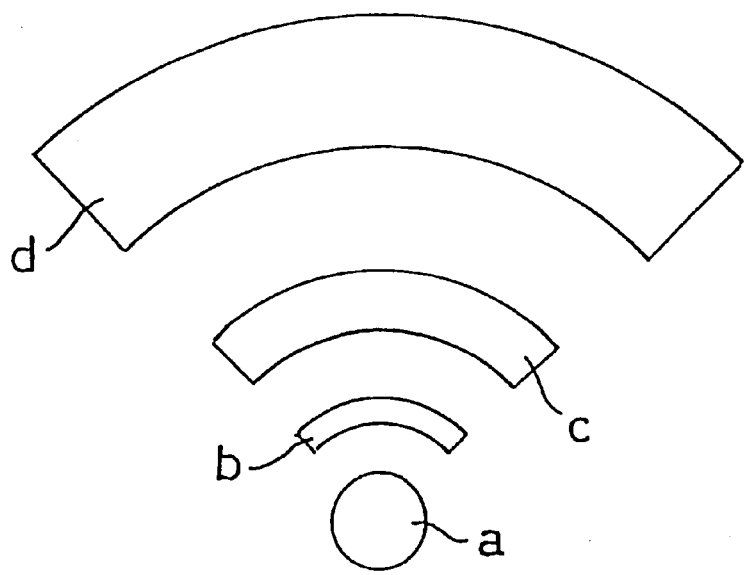
FIG. 5 is a plan view showing a conventional arrangement of light receiving elements.

The cross section of the light receiving element E constituting the photo detector 17 is shown in FIG. 1, wherein numeral 1 denotes the P layer, 1a an interface, 2 the N layer, 3 the N+ layer, 4 a depletion layer, 5 a positive electrode which serves as a support structure, 6 an insulation layer, 7 a negative electrode, M a masking for framing an effective light receiving area of the P layer 1, W its aperture, and K the aperture edge. Light receiving elements $E_1$, . . . are arranged, for example, in FIG. 3, but are not limited to this configuration. The cross-sectional drawing schematically shows one example with the light receiving element cut in the minor axis direction of the aperture W which will form an oblong circular arc, and for example, the positive electrode 5 setting position with its terminal for outputting a signal or the size of the aperture W with respect to the P layer 1 are not limited by the drawing.

The above-mentioned masking M is formed of an aluminum coating, for example, deposited by evaporation, etc. to the light receiving surface (insulation layer 6) of the light receiving element E and forms by etching an aperture W with a specified shape accuracy at a place corresponding to the P layer 1 of each light receiving element E, thereby ensuring easy fabrication. Because the aluminum material absorbs or reflects 100% of the incident light, the aperture W only can be used for the light receiving portion.

The shape accuracy of the aperture W formed by such masking M can be extremely high, and even if the shape accuracy of the P layer 1 is low, it is still possible to provide a highly accurate setting of the effective light receiving area (M). Consequently, since it is possible to arrange high shape accuracy light receiving elements E at a position near the center portion of the detector, downsizing can be achieved, and at the same time, improvement in measurement accuracy and expansion of the measuring area become possible.

Formation of the above-mentioned masking M can be achieved in one single process for all the light receiving elements $E_1$, . . . of the detector, and even if the location of the masking M is slightly deviated, there is no relative change in the location of each aperture $W_1$. . . , and therefore, the accuracy of isolation gap and alignment between light receiving elements can be improved, and it has been confirmed that the relative positional accuracy between light receiving portions (aperture W) can be reproducible at 0.5 μm or lower, and accuracy variations between detectors can be suppressed to a minimum, thereby enabling easy quality control and achieving uniformity of performance and quality.

As described above, because according to the photo detector of this invention, masking is provided with apertures for setting specified light receiving areas corresponding to each light receiving element is applied to the light receiving surface, the effective light receiving area of each light receiving element and isolation gap, alignment, etc. between light receiving elements can be set at a high accuracy, and light receiving elements with high shape accuracy can be arranged at a position close to the center portion of the detector, thereby enabling the achievement of downsizing, improvement in measuring accuracy, and expansion of the measuring area. Because uniform shape accuracy can be achieved by masking, improvement and uniformity of the quality and accuracy of the detector can also be achieved.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In a particle size distribution measuring equipment for irradiating a sample with a light beam and measuring the resulting light distribution from the sample, the improvement comprising:

a support structure;

a photo detector layer positioned on the support structure and providing a plurality of photo diodes;

an opaque coating deposited on the photo detector layer having a plurality of apertures of a high degree of accuracy to define a precise position of each aperture, each aperture is positioned across one of the photo diodes and covers a portion of that photo diode; and means for measuring the photo detector current corresponding to each aperture.

2. The particle size distribution measuring equipment of claim 1 wherein the opaque coating is aluminum film.

3. The particle size distribution measuring equipment of claim 1, wherein the apertures include at least a pair of arcs of about a concentric center.

4. In a particle size distribution measuring equipment for irradiating a sample with a light beam and measuring the resulting light distribution from the sample, the improvement comprising:

a support structure;

a photo detector layer positioned on the support structure and providing a plurality of radially spaced photo diodes;

an aluminum coating deposited across the entire photo detector layer having a plurality of are apertures positioned with a high degree of accuracy radially outward from a concentric center to define a precise position of each aperture, each aperture is positioned across one of the photo diodes and covers a portion of that photo diode; and terminal means for removing the photo detector current corresponding to each aperture.

5. In a particle size distribution measuring equipment for irradiating a sample with a light beam and measuring the resulting light distribution from the sample, the improvement comprising:

a unitary photo detector having a plurality of photo diodes spaced and aligned on a common surface, each photo diode having its own positive electrode terminal for providing an output signal representative of the light distribution received by that photo diode during a measurement cycle; and an opaque coating deposited directly on the photo detector with a plurality of apertures, each aperture positioned across one of the plurality of photo diodes and covering along a periphery of the aperture a portion of that photo diode.

6. The particle size distribution measuring equipment of claim 5 wherein the opaque coating extends across the positive electrode terminal.

7. The particle size distribution measuring equipment of claim 6 wherein the opaque coating is an aluminum film.

8. The particle size distribution measuring equipment of claim 7, wherein the apertures include at least a pair of arcs about a concentric center of the photo detector and a circular aperture at the concentric center.

9. The particle size distribution measuring equipment of claim 8 wherein a radial thickness of the arcs increase in dimension the further from the concentric center.

10. The particle size distribution measuring equipment of claim 9 wherein an insulation layer is positioned between each photo diode and the opaque coating, the apertures are etched to provide an accuracy, in the relative positions of each pair of arcs, of at least 0.5 µm.

* * * * *